(12) United States Patent
Tsai et al.

(10) Patent No.: US 9,198,969 B2
(45) Date of Patent: Dec. 1, 2015

(54) STABLE PHARMACEUTICAL FORMULATION OF CABAZITAXEL

(71) Applicant: Yung Shin Pharm. Ind. Co., Ltd., Tachia, Taichung (TW)

(72) Inventors: Chiung Ju Tsai, Miaoli County (TW); Shin Hong Jang, Miaoli County (TW); Tsang-Miao Huang, Changhua (TW); Jhih Li He, Chiayi County (TW)

(73) Assignee: YUNG SHIN PHARM. IND. CO., LTD., Tachia Taichung (TW)

( * ) Notice: Subject to any disclaimer, the term of this patent is extended or adjusted under 35 U.S.C. 154(b) by 0 days.

(21) Appl. No.: 13/967,822

(22) Filed: Aug. 15, 2013

(65) Prior Publication Data

US 2014/0171495 A1 Jun. 19, 2014

Related U.S. Application Data

(60) Provisional application No. 61/683,555, filed on Aug. 15, 2012.

(51) Int. Cl.
| | |
|---|---|
| *A61K 47/02* | (2006.01) |
| *A61K 31/337* | (2006.01) |
| *A61K 47/10* | (2006.01) |
| *A61K 9/00* | (2006.01) |
| *A61K 47/26* | (2006.01) |

(52) U.S. Cl.
CPC ............... *A61K 47/02* (2013.01); *A61K 9/0095* (2013.01); *A61K 31/337* (2013.01); *A61K 47/10* (2013.01); *A61K 47/26* (2013.01)

(58) Field of Classification Search
USPC .......................................................... 514/449
See application file for complete search history.

(56) References Cited

U.S. PATENT DOCUMENTS

| | | | | |
|---|---|---|---|---|
| 5,504,102 | A * | 4/1996 | Agharkar et al. | 514/449 |
| 7,589,106 | B2 * | 9/2009 | Palepu | 514/314 |
| 2005/0065138 | A1 | 3/2005 | Didier | |
| 2006/0111432 | A1 * | 5/2006 | Lee et al. | 514/449 |
| 2012/0048418 | A1 | 3/2012 | Giribona et al. | |
| 2012/0065255 | A1 | 3/2012 | Palepu | |

FOREIGN PATENT DOCUMENTS

| | | |
|---|---|---|
| WO | WO 2007/020085 | 2/2007 |
| WO | WO 2009/115655 | 9/2009 |

OTHER PUBLICATIONS

International Search Report and Written Opinion of International Patent Application No. PCT/US2013/055083 with a mailing date of Nov. 28, 2013.
Product Insert: JEVTANA (cabazitaxel) Injection (May 2013).

\* cited by examiner

*Primary Examiner* — Kathrien Cruz
(74) *Attorney, Agent, or Firm* — Perkins Coie LLP; Viola T. Kung

(57) ABSTRACT

The present invention relates to a stable liquid cabazitaxel formulation in an enclosed container. The enclosed container comprises a liquid phase and an gaseous phase, wherein the liquid phase comprises cabazitaxel, polysorbate 80, ethanol, and one or more pH adjusters to maintain pH about 2.8-6.0, and the gaseous phase is saturated with $CO_2$. The present invention is also directed to a process for preparing the enclosed liquid pharmaceutical composition container.

12 Claims, 2 Drawing Sheets

STABLE PHARMACEUTICAL FORMULATION OF CABAZITAXEL

The present application claims priority to U.S. Provisional Application No. 61/683,555, filed on Aug. 15, 2012, which is incorporated herein by reference in its entirety.

TECHNICAL FIELD

The present invention relates to a stable liquid cabazitaxel formulation. The formulation comprises cabazitaxel, polysorbate, alcohol, and a pH adjusting agent. The liquid cabazitaxel formulation is contained in an enclosed container and is saturated with gaseous $CO_2$.

BACKGROUND

Cabazitaxel was developed by Sanofi-Aventis and was approved by FDA in 2010. JEVTANA® (cabazitaxel) is a microtubule inhibitor indicated in combination with prednisone for the treatment of patients with hormone-refractory metastatic prostate cancer previously treated with a docetaxel-containing treatment regimen.

Cabazitaxel is an anti-neoplastic agent belonging to the taxane class. It is prepared by semi-synthesis with a precursor extracted from yew needles. The chemical name of cabazitaxel is $(2\alpha,5\beta,7\beta,10\beta,13\alpha)$-4-acetoxy-13-({(2R,3S)-3[(tertbutoxycarbonyl)amino]-2-hydroxy-3-phenylpropanoyl}oxy)-1-hydroxy-7,10-dimethoxy-9-oxo-5,20-epoxytax-11-en-2-yl benzoate-propan-2-one(1:1). Its chemical structure is shown below.

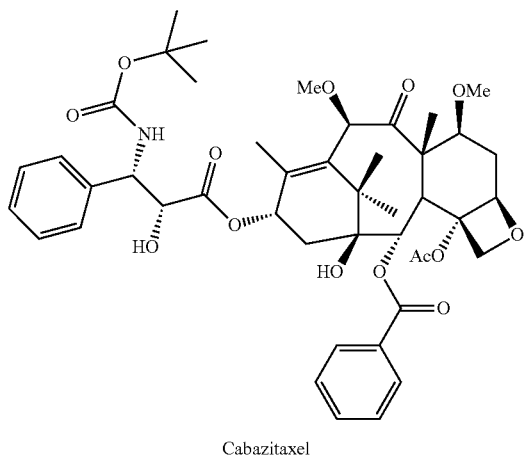

Cabazitaxel

Cabazitaxel is a white to off-white powder with a molecular weight of 894.01 (for the acetone solvate)/835.93 (for solvent free). Cabazitaxel is known to have poor solubility in water or general pharmaceutical solvents. It is lipophilic, soluble in alcohol, but practically insoluble in water. JEVTANA® (cabazitaxel) Injection (60 mg/1.5 mL) is a sterile, non-pyrogenic, clear yellow to brownish-yellow viscous solution and is available in a single-use vial containing 60 mg cabazitaxel (anhydrous and solvent free) and 1.56 g polysorbate 80. Each mL contains 40 mg cabazitaxel (anhydrous) and 1.04 g polysorbate 80. JEVTANA® Injection requires two dilutions prior to administration.

Diluent for JEVTANA® is a clear, colorless, sterile, and non-pyrogenic solution containing 13% (w/w) ethanol in water for injection, approximately 5.7 mL. JEVTANA® Injection is first diluted with a supplied Diluent for JEVTANA®, followed by a second dilution in either 0.9% sodium chloride solution or 5% dextrose solution for administering to a patient. First diluted solution of JEVTANA® should be used immediately (within 30 minutes) for preparing the second diluted injectable solution. Both JEVTANA® Injection and Diluent should be stored at 25° C. (permitted between 15-30° C.), and should not be refrigerated.

The complexity of preparing two dilutions of a cabazitaxel injection solution for use is inconvenient and increases the risk of bacteria infection.

There is a need for a single-vial and stable formulation for cabazitaxel, which can be diluted once for intravenous infusion.

SUMMARY OF THE INVENTION

The present invention is directed to an enclosed liquid pharmaceutical composition container, comprising a liquid phase and an gaseous phase, wherein the liquid phase comprises cabazitaxel, polysorbate 80, ethanol, and one or more pH adjusters to maintain pH about 2.8-6.0, and the gaseous phase is saturated with $CO_2$.

The present invention is also directed to a process for preparing the enclosed liquid pharmaceutical composition container. The process comprises the steps of: (a) mixing cabazitaxel, polysorbate 80, one or more pH adjusters, and ethanol to prepare a liquid pharmaceutical formulation, (b) filing the formulation into a container, (c) adding a sufficient amount of gaseous $CO_2$ to occupy the open space of the container, and (d) sealing the container.

DETAILED DESCRIPTION OF THE INVENTION

A Liquid Pharmaceutical Composition

Figure 1:
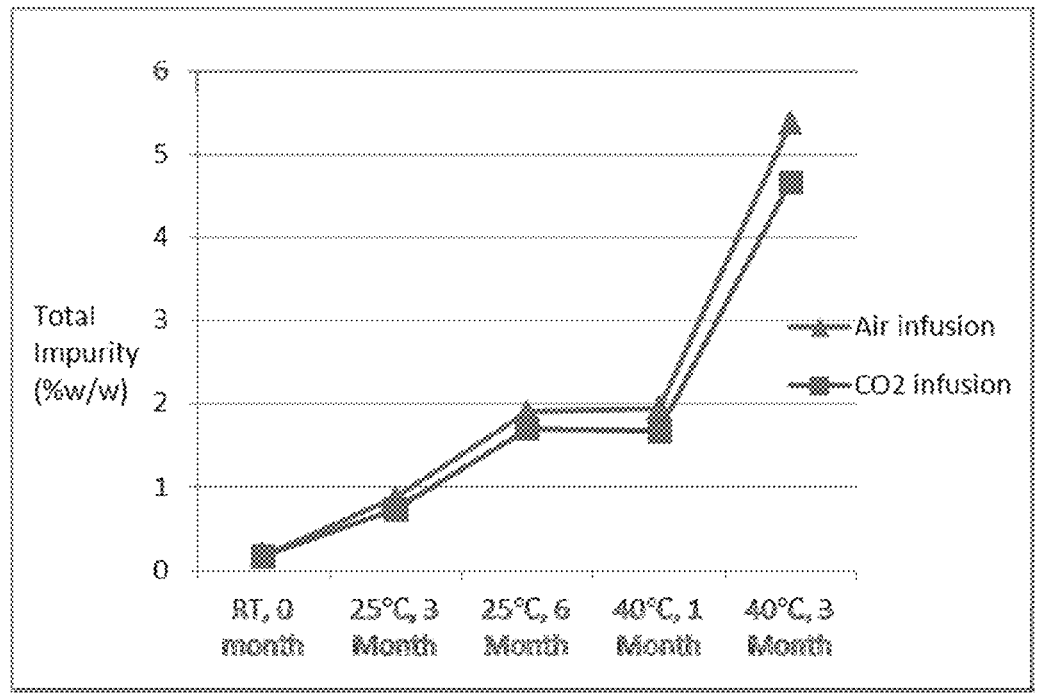
FIG. 1 shows the comparative stability data at room temperature and 40° C. for air-infused vs. $CO_2$-infused Formulation RE024 (no citric acid).

The present invention is directed to a liquid pharmaceutical composition comprising cabazitaxel, polysorbate, ethanol, and a pH adjuster; at pH 3-6.

The amount of cabazitaxel in the pharmaceutical composition is about 0.1-10% by weight, preferably 0.05-5%, more preferably 1-2%.

"About" as used in this application, refers to ±5% of the recited value.

The volume of the alcohol is about 20-60% of the pharmaceutical composition. A preferred alcohol is 95% ethanol or dehydrated ethanol (>99.5% and <0.2% moisture).

The amount of polysorbate is about 20-60% or 40-60%, for example, 26% or 52% (w/v), of the pharmaceutical composition. A preferred polysorbate is polysorbate 80 (TWEEN® 80).

One or more pH adjusters, such as carbonic acid/carbonate, citric acid/citrate, or acetic acid/acetate, which maintain pH between about 3 to 6, preferably pH between about 3 to 5, or between about 3 to 4.5, can be used in the formulation.

One preferred pH adjuster is carbonic acid/carbonate, prepared by infusing $CO_2$ into water or alcohol. The amount of $CO_2$ should be sufficient to lower the pH of the injectable aqueous solution to about ≤5.0, or about ≤4.0, and is at least about 0.4 mL of saturated $CO_2$ solution per mL of the pharmaceutical composition. A suitable form of $CO_2$ used in the preparation is dry ice or $CO_2$ gas or a mixture of both.

Another preferred pH adjuster is citric acid/citrate. A suitable amount of citrate or citric acid is about 1-10 mg/mL, preferably 2-8 mg/mL, or 3-6 mg/mL, which can be used alone or in combination with carbonate.

The injectable pharmaceutical composition is preferably filtered (through 0.22µ) to sterilize the composition. The sterilized injectable pharmaceutical composition is then filled into a vial. An adequate amount of $CO_2$ gas, is then infused into the residual space of the vial so as to further saturate the injectable pharmaceutical composition and maintaining its acidity before sealing of the vial.

The present invention is directed to an enclosed container containing the liquid cabazitaxel composition as described above and infused $CO_2$ gas occupying the residual space of the container. Any sealed container such as a vial or a tube is suitable for the present invention.

The present invention is directed to an enclosed liquid pharmaceutical composition container, comprising a liquid phase and an gaseous phase, wherein the liquid phase the liquid pharmaceutical formulation as described above, and the gaseous phase is saturated with $CO_2$.

Method of Preparing Cabazitaxel

Crystalline forms of cabazitaxel can be purchased from several commercial sources, e.g., MedKoo Biosciences. Alternatively, a crystalline form of cabazitaxel can be prepared according to US2012/0149925, which is incorporated herein by reference in its entirety.

An amorphous form cabazitaxel can be prepared by a method comprising (a) dissolving a solid form of cabazitaxel in an organic solvent or a solvent mixture, and (b) removing the organic solvent or the solvent mixture to form the compound. The solvent and the solvent mixture are selected from the group consisting of dichloromethane, ethanol, methanol, acetone, ethyl acetate, isopropyl alcohol, toluene, chloroform, dimethylformamide, dimethylacetamide, dimethylsulfoxide, methylene chloride, acetonitrile, and a combination thereof. The solvent or solvent mixture of the above method can be removed by evaporation, vacuum condensation, spray drying, or filtration and drying. In one embodiment, the solvent or solvent mixture is removed, for example, by vacuum condensation, at about 25-60° C., and under a pressure less than about 700 mm Hg, preferably less than about 300 or 100 mmHg. In another embodiment, the solvent or solvent mixture is removed by spray drying with nitrogen gas having an inlet temperature of about 50-150° C. In another embodiment, the solvent or solvent mixture is removed by drying under reduced pressure at about 40° C. The process of removing the solvent in general takes place quickly to avoid orderly crystal growth, in about 1-60 minutes, or 3-30 minutes, or 5-10 minutes.

Cabazitaxel, either in a crystalline form or in an amorphous form, can be used to prepare the liquid pharmaceutical formulation of the present invention.

Single-Container Liquid Cabazitaxel Formulation

The present invention is also directed to a single-container, liquid cabazitaxel formulation. The single-container formulation is ready to be diluted once and administered to a patient, which eliminates one extra dilution procedure of JEVTANA®. The vial contains the liquid injectable pharmaceutical composition as described above. The container (e.g., a vial) has two phases, a liquid phase (the injectable pharmaceutical composition), and a gas phase (the space within the vial that is not occupied by the liquid phase).

After the injectable pharmaceutical composition is filled into a vial, an adequate amount of $CO_2$ gas is infused into the residual space of the vial so as to further saturate the injectable pharmaceutical composition and maintaining its acidity to about pH 2.8-6.0, preferably about pH 3.0-4.5, or about pH 3.0-4.0, before sealing of the vial.

The hydroxyl groups in cabazitaxel are much easier to be oxidized than other functional groups; and the oxidation of hydroxyl group in cabazitaxel causes the main impurities in the composition. Addition of $CO_2$ in the vial has an advantage of decreasing the content of $O_2$ in both the liquid and the gas phases of the vial. Because the content of $O_2$ in the liquid phase is the key factor that leads to the oxidation of hydroxyl function groups on cabazitaxel, decreased content of $O_2$ in the liquid phase lowers the undesired oxidation on cabazitaxel and provides cabazitaxel with better stability.

$CO_2$ is heavier than other main gases such as oxygen and nitrogen in the atmosphere. When a higher density gas ($CO_2$) is added into the vial, $CO_2$ reaches down to the liquid-gas interface and pushes the lower density gas ($O_2$) up from the liquid-gas interface. When the vial is not sealed, the lower density gas ($O_2$) is expelled from the vial by the higher density gas ($CO_2$). Addition of $CO_2$ may also lower the content of $O_2$ in the liquid phase due to the equilibrium between the content of $O_2$ in the liquid phase and in the gas phase.

Methods for Preparing Single-Container Liquid Cabazitaxel Formulation

The present application is directed to a method for preparing a single-container, liquid cabazitaxel formulation in an enclosed container. The liquid cabazitaxel formulation in the single vial is stable and is ready to be diluted once and administered to a patient. The method comprises the steps of: (a) mixing cabazitaxel, polysorbate, one or more pH adjusters, and ethanol in any order to prepare a pharmaceutical formulation, (b) filing the pharmaceutical formulation into a container such as a vial, (c) adding a sufficient amount of gaseous $CO_2$ to occupy the open space of the container, and (d) sealing the container; whereby the sealed container contains the liquid pharmaceutical formulation and the gaseous $CO_2$.

In one embodiment, a pH adjuster of carbonic acid/carbonate is first prepared by adding a sufficient amount of gaseous $CO_2$ to water until the pH reaches about ≤5 (e.g. pH about 3-5) or about ≤4 (e.g., pH about 3-4).

In one embodiment, a pH adjuster is citrate acid/citrate.

In one embodiment, the pH adjusters are carbonic acid/carbonate and citrate acid/citrate.

In one embodiment, a first pH adjuster of carbonic acid is first prepared as described above, then polysorbate 80 is added to the above mixture. Then cabazitaxel, citric acid, and alcohol is added to the mixture.

In other embodiments, the addition of polysorbate, alcohol, citric acid, and cabazitaxel can be in any order. For example, a pH adjuster of carbonic acid is first prepared as described above. Then polysorbate 80 and a sufficient amount of alcohol is added to the above mixture. Then cabazitaxel and alcohol is added to the mixture.

In another embodiment, a first pH adjuster of carbonic acid is first prepared as described above. A proper amount of a second pH adjuster citric acid and cabazitaxel are mixed with the aqueous $CO_2$ solution until they are dissolved. Then polysorbate 80 and a sufficient amount of alcohol is added to the above mixture.

The final liquid mixture is optionally filtered through 0.22µ filter and then filled into a vial, gas $CO_2$ is infused into the unoccupied space of the vial, and the vial is sealed. $CO_2$ gas cylinder or dry ice can be used to provide gaseous $CO_2$. A sufficient amount of $CO_2$ is added to completely occupy the gaseous space in the vial. For example, $CO_2$ is infused into a 1-10 mL vial for 1-10 minutes, or 3-6 minutes, or 5-10 minutes, or at least 5 minutes, to saturate the gaseous phase and the liquid phase.

The injectable pharmaceutical composition of the present invention is suitable for treating patients with cancer, such as breast cancer, ovarian cancer, lung cancer, melanoma, prostate cancer and lymphoma.

EXAMPLES

Example 1

Preparation of 7,10-di-methoxy-10-deacetylbaccatin (III) (C1) catalyzed by CsBr

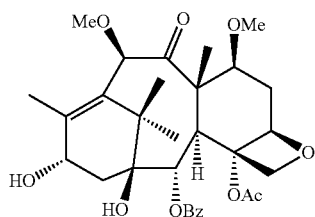

A solution of sodium hydride (60%, 3 eq, 0.22 g)/CsBr (0.5 eq, 0.20 g) was dissolved in co-solvent THF/DMF (2/1, 6 mL), cooled down to −20° C. under nitrogen, and stirred for 20 minutes. Natural taxoid 10-deacetylbaccatin III (10-DAB) was obtained from Yung Shin Pharm. Ind. Co. LTD. (Taichung, Taiwan) or SM Herbal (India). 10-DAB (1 eq, 1 g)/$Me_2SO_4$ (10 eq, 1.74 mL) in THF/DMF (2/1, 6 mL) was added into the sodium hydride reaction mixture slowly. The reaction mixture was allowed to warm up to room temperature gradually. The reaction mixture was stirred for 2 hours until the reaction was completed. The mixture was quenched with 10% AcOH/THF, and extracted with $CH_2Cl_2$ and water. After partition, the organic layer extracted with saturated $NaHCO_{3(aq)}$. It was concentrated and purification by recrystallization ($CH_2Cl_2$/Hexane) to yielded C1 as white solid (yield: 50%, 0.37 g, LC purity: 90%). $^1$H NMR (400 MHz, $D^6$-DMSO) δ 8.01 (d, J=7.2 Hz, 2H), 7.66 (t, J=7.4 Hz, 1H), 7.56 (t, J=7.6 Hz, 2H), 5.37 (d, J=7.2 Hz, 1H), 5.31 (d, J=4.0 Hz, 1H), 4.97 (d, J=8.4 Hz, 1H), 4.74 (s, 1H), 4.72-4.61 (m, 1H), 4.40 (s, 1H), 4.03 (dd, J=8.2, 13.4 Hz, 2H), 3.81 (dd, J=6.6, 10.6 Hz, 1H), 3.75 (d, J=7.2 Hz, 1H), 3.29 (s, 3H), 3.21 (s, 3H), 2.74-2.62 (m, 1H), 2.20 (s, 3H), 2.17 (d, J=8.4 Hz, 2H), 1.97 (s, 3H), 1.58-1.41 (m, 4H), 0.93 (s, 6H); $^{13}$C NMR (100 MHz, $D^6$-DMSO) δ 205.5, 169.7, 165.2, 144.1, 133.3, 132.8, 130.2, 129.5, 128.7, 83.3, 82.8, 80.5, 80.1, 76.9, 75.3, 74.4, 66.2, 56.7, 56.5, 56.1, 47.1, 42.5, 31.8, 26.9, 22.4, 20.5, 15.2, 10.1.

Example 2

Preparation of 1-hydroxy-7β,10β-di-methoxy-9-oxo-5β,20-epoxytax-11-ene-2α,4,13α-triyl 4-acetate 2-benzoate 13-{(2R,3S)-3-[(tert-butoxycarbonyl)amino]-2-trethylsilyloxy-3-phenylpropanoate} (C2) by the catalyst of LiBr

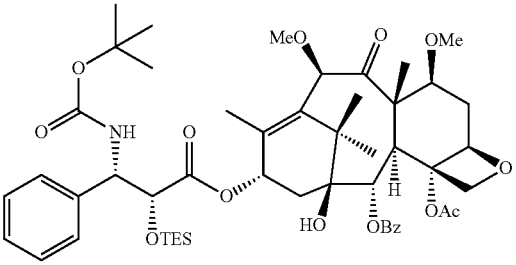

A solution of sodium hydride (60%, 8 eq, 112 mg) was dissolved in 2 mL THF and cooled down to −15° C. under nitrogen. And then 7,10-di-methoxy-10-DAB C1 (1 eq, 200 mg) dissolved in 2 mL THF was added into the sodium hydride mixture. And then was added the mixture of (3R,4S)-tert-butyl-2-oxy-4-phenyl-3-(triethylsilyloxy)azetidine-1-carboxylate (2.5 eq, 329 mg) and LiBr (0.5 eq, 15 mg) in 2 mL THF slowly. The reaction mixture was stirred 2 hours at −15~20° C. until the reaction was complete. The mixture was quenched with 10% AcOH/THF, and extracted with ethylacetate and water. The organic layer was dried by rotavapor to obtain the crude C2 (LC purity: 58%); $^1$H NMR (400 MHz, $CDCl_3$) δ 8.10 (d, J=7.2 Hz, 2H), 7.58 (t, J=7.4 Hz, 1H), 7.47 (t, J=7.6 Hz, 2H), 7.37 (t, J=7.4 Hz, 2H), 7.32-7.27 (m, 3H), 6.29 (t, J=8.6 Hz, 1H), 5.65 (d, J=7.2 Hz, 1H), 5.49 (d, J=9.6 Hz, 1H), 5.27 (d, J=10.0 Hz, 1H), 5.00 (d, J=7.6 Hz, 1H), 4.80 (s, 1H), 4.55 (s, 1H), 4.25 (dd, J=8.4, 52.0 Hz, 2H), 3.94-3.83 (m, 2H), 3.45 (s, 3H), 3.30 (s, 3H), 2.76-2.65 (m, 1H), 2.53 (s, 3H), 2.41-2.14 (m, 2H), 1.95 (s, 3H), 1.85-1.74 (m, 2H), 1.72 (s, 3H), 1.68 (s, 1H), 1.33 (s, 9H), 1.24 (s, 3H), 1.20 (s, 3H), 0.78 (t, J=7.8 Hz, 9H), 0.49-0.28 (m, 6H); $^{13}$C NMR (100 MHz, $CDCl_3$) δ 204.9, 171.7, 170.0, 166.9, 155.2, 139.4, 138.9, 135.0, 133.5, 130.1, 129.2, 128.6, 128.5, 127.7, 126.4, 84.1, 82.4, 81.5, 80.6, 79.8, 78.9, 76.4, 75.2, 74.8, 71.6, 57.2, 57.0, 56.7, 47.2, 43.3, 35.2, 31.9, 28.1, 26.6, 22.9, 21.2, 14.3, 10.3, 6.5, 4.2.

Example 3

Preparation of (2α,5β,7β,10β,13α)-4-acetoxy-13-({(2R,3S)-3[(tertbutoxycarbonyl)amino]-2-hydroxy-3-phenylpropanoyl}oxy)-1-hydroxy-7,10-dimethoxy-9-oxo-5,20-epoxytax-11-en-2-ylbenzoate-propan-2-one(1:1) (Cabazitaxel)

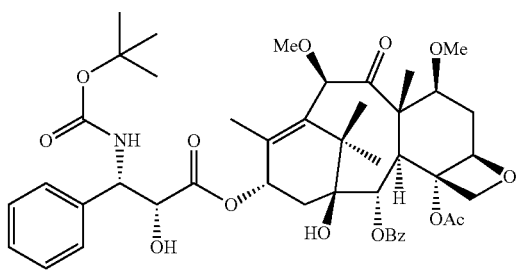

Cabazitaxel

The C2 (490 mg, 1 eq) was dissolved in 3.5 mL MeOH and was added dropwise 32% $HCl_{(aq)}$ at −5~5° C., until the pH of C2 mixture reached between 1-2. The reaction mixture was stirred at −5~5° C. until the deprotection was completed, then it was quenched with saturated $NaHCO_{3(aq)}$ and extracted with $CH_2Cl_2$. The organic layer was concentrated and purification by recrystallization ($CH_2Cl_2$/Hexane) to yielded cabazitaxel as white solid (yield: 65%; 280 mg, LC purity: 98%).
$^1H$ NMR (400 MHz, $CDCl_3$) δ 8.09 (d, J=7.6 Hz, 2H), 7.60 (t, J=7.4 Hz, 1H), 7.48 (t, J=8.0 Hz, 2H), 7.42-7.36 (m, 4H), 7.36-7.29 (m, 1H), 6.20 (t, J=8.6 Hz, 1H), 5.63 (d, J=7.2 Hz, 1H), 5.43 (d, J=9.6 Hz, 1H), 5.26 (d, J=8.8 Hz, 1H), 4.97 (d, J=8.0 Hz, 1H), 4.79 (s, 1H), 4.62 (s, 1H), 4.23 (dd, J=8.2, 50.0 Hz, 2H), 3.90-3.77 (m, 2H), 3.50-3.40 (m, 4H), 3.30 (s, 3H), 2.75-2.64 (m, 1H), 2.36 (s, 3H), 2.32-2.18 (m, 2H), 1.88 (s, 3H), 1.84-1.74 (m, 2H), 1.71 (s, 3H), 1.67 (s, 1H), 1.36 (s, 9H), 1.23-1.17 (m, 6H); $^{13}C$ NMR (100 MHz, $CDCl_3$) δ 204.9, 172.6, 170.3, 166.8, 155.3, 138.7, 138.3, 135.4, 133.6, 130.1, 129.1, 128.7, 128.6, 127.9, 126.7, 84.0, 82.5, 81.6, 80.7, 80.1, 78.6, 76.4, 74.5, 73.7, 72.4, 57.2, 57.0, 56.8, 47.3, 43.2, 35.2, 32.0, 28.1, 26.7, 22.6, 20.6, 14.5, 10.3.

Example 4

Preparation of Amorphous Cabazitaxel

The cabazitaxel solid (in a crystalline form) of Example 3 was dissolved in dichloromethane (0.6 mL), ethanol (2.0 mL), methanol (0.6 mL), or acetone (0.8 mL), followed by concentration to dryness under reduced pressure (<100 mm Hg) at 40° C. for about 5-10 minutes.

The solid obtained was an amorphous form of cabazitaxel.

Cabazitaxel prepared from Example 3 or 4 is used in Examples 5-11.

Example 5

Preparation of a Liquid Cabazitaxel Formulation

| (A) | Composition | Amount |
| --- | --- | --- |
| 1. | Cabazitaxel | 20 mg/10 mg |
| 2. | Polysorbate 80 | 520 mg/260 mg |
| 3. | Alcohol | q.s. |
| 4. | Citric acid | 3 mg |
|  | Total Volume | 1 mL |

"q.s."* = "quantum sufficiat", the Latin term, which is frequently used in medicine and pharmacy, means "a sufficient quantity".

(B) Preparing Steps:
 (1) To premix a sufficient quantity of alcohol and 3 mg citric acid first and then add 520 mg/260 mg polysorbate 80 into the mixture.
 (2) To add 20 mg/10 mg cabazitaxel into (1) and mix, and then add a sufficient quantity of alcohol into the mixture to 1 mL.

Example 6

Preparation of a Liquid Cabazitaxel Formulation

| (A) | Composition | Amount |
| --- | --- | --- |
| 1. | Cabazitaxel | 20 mg/10 mg |
| 2. | Polysorbate 80 | 520 mg/260 mg |
| 3. | Alcohol | q.s. |
| 4. | Citric acid | 6 mg |
|  | Total Volume | 1 mL |

(B) Preparing steps:
 (1) To premix a sufficient quantity of alcohol and 6 mg citric acid first and then add 520 mg/260 mg polysorbate 80 into the mixture.
 (2) To add 20 mg/10 mg cabazitaxel into (1) and mix, and then add a sufficient quantity of alcohol into the mixture to 1 mL.

Example 7

Preparation of a Liquid Cabazitaxel Formulation

| (A) | Composition | Amount |
| --- | --- | --- |
| 1. | Cabazitaxel | 20 mg/10 mg |
| 2. | Polysorbate 80 | 520 mg/260 mg |
| 3. | Alcohol | q.s. |
| 4. | $CO_2$ | q.s. |
| 5. | water | 0.04 mL |
|  | Total Volume | 1 mL |

(B) Preparing Steps:
 (1) To premix a sufficient quantity of carbon dioxide into water first until the pH is ≤5, and then take 0.04 mL of the premixed water ready for use in (2).
 (2) To add a sufficient quantity of alcohol and 520 mg/260 mg polysorbate 80 into the premixed water of (1) and stir the solution until the solids are dissolved.
 (3) To add 20 mg/10 mg cabazitaxel into (2) and mix, and then add a sufficient quantity of alcohol into the mixture to 1 mL.

Example 8

Preparation of a Liquid Cabazitaxel Formulation

| (A) | Composition | Amount |
| --- | --- | --- |
| 1. | Cabazitaxel | 20 mg/10 mg |
| 2. | Polysorbate 80 | 520 mg/260 mg |
| 3. | Alcohol | q.s. |
| 4. | $CO_2$ | q.s. |
| 5 | Citric acid | 3 mg |
|  | Total Volume | 1 mL |

(B) Preparing Steps:
 (1) To add a sufficient quantity carbon of dioxide into alcohol until the pH is ≤5.
 (2) To add 3 mg citric acid and 20 mg/10 mg cabazitaxel step by step into (1) and stir the solution until the solids are dissolved.
 (3) To add 520 mg/260 mg polysorbate 80 into (2) and mix. Add a sufficient quantity of alcohol into the mixture to 1 mL.
 (4) To fill the mixture of (3) into a vial first and then infuse carbon dioxide into the unoccupied space of the vial.

Example 9

Preparation of a Liquid Cabazitaxel Formulation

| (A) | Composition | Amount |
|---|---|---|
| 1. | Cabazitaxel | 20 mg/10 mg |
| 2. | Polysorbate 80 | 520 mg/260 mg |
| 3. | Alcohol | q.s. |
| 4. | $CO_2$ | q.s. |
| 5 | Citric acid | 6 mg |
|   | Total Volume | 1 mL |

(B) Preparing Steps:
 (1) To add a sufficient quantity carbon of dioxide into alcohol until the pH value≤5.
 (2) To add 6 mg citric acid and 20 mg/10 mg cabazitaxel step by step into (1) and stir the solution until the solids are dissolved.
 (3) To add 520 mg/260 mg polysorbate 80 into (2) to mix. Add a sufficient quantity of alcohol into the mixture to 1 mL.
 (4) To fill the mixture of (3) into a vial first and then infuse carbon dioxide into the unoccupied space of the vial.

Example 10

Preparation of a Liquid Cabazitaxel Formulation

| (A) | Composition | Amount |
|---|---|---|
| 1. | Cabazitaxel | 20 mg/10 mg |
| 2. | Polysorbate 80 | 520 mg/260 mg |
| 3. | Alcohol | q.s. |
| 4. | $CO_2$ | q.s. |
| 5. | water | 0.04 mL |
| 6 | Citric acid | 3 mg |
|   | Total Volume | 1 mL |

(B) Preparing Steps:
 (1) To premix a sufficient quantity of carbon dioxide into water first until the pH is ≤5, and then take 0.04 mL of the premixed water ready for use in (2).
 (2) To add 3 mg citric acid and 20 mg/10 mg cabazitaxel step by step into the premixed water of (1) and stir the solution until the solids are dissolved.
 (3) To add 520 mg/260 mg Polysorbate 80 into (2) to mix. Add a sufficient quantity of alcohol into the mixture to 1 mL.
 (4) To fill the mixture of (3) into a vial first and then infuse carbon dioxide into the unoccupied space of the vial.

Example 11

Preparation of a Liquid Cabazitaxel Formulation

| (A) | Composition | Amount |
|---|---|---|
| 1. | Cabazitaxel | 20 mg/10 mg |
| 2. | Polysorbate 80 | 520 mg/260 mg |
| 3. | Alcohol | q.s. |
| 4. | $CO_2$ | q.s. |
| 5. | water | 0.04 mL |
| 6 | Citric acid | 6 mg |
|   | Total Volume | 1 mL |

(B) Preparing Steps:
 (1) To premix a sufficient quantity of carbon dioxide into water first until the pH is ≤5, and then take 0.04 mL of the premixed water ready for use in (2).
 (2) To add 6 mg citric acid and 20 mg/10 mg cabazitaxel step by step into the premixed water of (1) and stir the solution until the solids are dissolved.
 (3) To add 520 mg/260 mg Polysorbate 80 into (2) to mix. Add a sufficient quantity of alcohol into the mixture to 1 mL.
 (4) To fill the mixture of (3) into a vial first and then infuse carbon dioxide into the unoccupied space of the vial.

Example 12

Preparation of Formulations RE018-026

(A) Composition
The compositions of Formulations RE018-026 are summarized in Table 1.

TABLE 1

|  | Cabazitaxel | Polysorbate 80 | Citric Acid Anhydrate | Water ($CO_2$ fusion; pH ≤ 4) | Dehydrate Ethanol addition | pH air infusion | pH $CO_2$ infusion |
|---|---|---|---|---|---|---|---|
| RE018 | 20 mg | 520 mg | — | 0.04 ml | to 1 ml | 6.5 | 5.2 |
| RE019 | 20 mg | 520 mg | 3 mg | 0.04 ml | to 1 ml | 3.4 | 3.4 |
| RE020 | 20 mg | 520 mg | 6 mg | 0.04 ml | to 1 ml | 3.0 | 3.0 |
| RE021 | 10 mg | 520 mg | — | 0.04 ml | to 1 ml | 5.7 | 5.5 |
| RE022 | 10 mg | 520 mg | 3 mg | 0.04 ml | to 1 ml | 3.4 | 3.4 |
| RE023 | 10 mg | 520 mg | 6 mg | 0.04 ml | to 1 ml | 3.0 | 3.0 |
| RE024 | 10 mg | 260 mg | — | 0.04 ml | to 1 ml | 6.0 | 5.0 |
| RE025 | 10 mg | 260 mg | 3 mg | 0.04 ml | to 1 ml | 3.2 | 3.1 |
| RE026 | 10 mg | 260 mg | 6 mg | 0.04 ml | to 1 ml | 2.9 | 2.9 |

(B) Preparing Steps:
 (1) A sufficient quantity of carbon dioxide was premixed into water until the pH is ≤4. The premixed water was ready for use in (3).
 (2) A sufficient quantity (<1 ml) of dehydrate alcohol was added to completely dissolve 20 mg/10 mg amorphous cabazitaxel (prepared according to Example 4) and 0 mg/3 mg/6 mg citric acid.

(3) 0.04 mL of the premixed water in the step (1) was mixed with 520 mg/260 mg polysorbate 80 and the solution stirred for complete mixing.
(4) The solutions in step (2) and (3) were completely mixed and then a sufficient quantity of dehydrate alcohol was added into the mixture to make a total volume of 1 mL.
(5) The mixture of (4) was filtered through 022μ and filled into a vial.
(6) For $CO_2$ infusion, gaseous carbon dioxide from a gas tank was added into the unoccupied space of the vial for at least 5 minutes and the vial was then sealed.

For air infusion, no extra step was taken, and the vial was sealed.

Example 13

Stability of Formulations RE018-026

Formulations RE018-026 were stored at 25° C. or 40° C., and % total impurities were measured at each specified time point. The total impurities include 10-deacetylbaccatin III, 7,10-di-methoxy-10-deacetylbaccatin (III), and some unspecified impurities. The results of % of total impurities are listed below in Tables 2-10.

TABLE 2

(% of Total Impurities)

| RE018 (No Citric acid) | Air infusion | $CO_2$ infusion |
|---|---|---|
| Starting Time | 0.3 | 0.27 |
| 25° C., 3 Month | 1.1 | 0.97 |
| 25° C., 6 Month | 2.3 | 2 |
| 40° C., 1 Month | 2.27 | 2.03 |
| 40° C., 3 Month | 5.15 | 5.62 |

TABLE 3

(% of Total Impurities)

| RE019 (Citric acid 3 mg) | Air infusion | $CO_2$ infusion |
|---|---|---|
| Starting Time | 0.1 | 0.17 |
| 25° C., 3 Month | 0.07 | 0.08 |
| 25° C., 6 Month | 0.2 | 0.2 |
| 40° C., 1 Month | 0.29 | 0.11 |
| 40° C., 3 Month | 0.57 | 0.31 |

TABLE 4

(% of Total Impurities)

| RE020 (Citric acid 6 mg) | Air infusion | $CO_2$ infusion |
|---|---|---|
| Starting Time | 0.19 | 0.24 |
| 25° C., 3 Month | 0.15 | 0.09 |
| 25° C., 6 Month | 0.2 | 0.2 |
| 40° C., 1 Month | 0.28 | 0.1 |
| 40° C., 3 Month | 0.65 | 0.36 |

TABLE 5

(% of Total Impurities)

| RE021 (No Citric acid) | Air infusion | $CO_2$ infusion |
|---|---|---|
| Starting Time | 0.22 | 0.2 |
| 25° C., 3 Month | 1.1 | 0.98 |
| 25° C., 6 Month | 2.3 | 2 |
| 40° C., 1 Month | 2.46 | 2.09 |
| 40° C., 3 Month | 5.22 | 5.86 |

TABLE 6

(% of Total Impurities)

| RE022 | Air infusion | $CO_2$ infusion |
|---|---|---|
| Starting Time | 0.06 | 0.06 |
| 25° C., 3 Month | 0.17 | 0.07 |
| 25° C., 6 Month | 0.2 | 0.1 |
| 40° C., 1 Month | 0.43 | 0.09 |
| 40° C., 3 Month | 0.73 | 0.25 |

TABLE 7

(% of Total Impurities)

| RE023 (Citric acid 6 mg) | Air infusion | $CO_2$ infusion |
|---|---|---|
| Starting Time | 0.42 | 0.06 |
| 25° C., 3 Month | 0.18 | 0.07 |
| 25° C., 6 Month | 0.1 | 0.1 |
| 40° C., 1 Month | 0.38 | 0.09 |
| 40° C., 3 Month | 0.74 | 0.25 |

TABLE 8

(% of Total Impurities)

| RE024 (No Citric acid) | Air infusion | $CO_2$ infusion |
|---|---|---|
| Starting Time | 0.18 | 0.17 |
| 25° C., 3 Month | 0.87 | 0.73 |
| 25° C., 6 Month | 1.9 | 1.7 |
| 40° C., 1 Month | 1.95 | 1.68 |
| 40° C., 3 Month | 5.38 | 4.67 |

TABLE 9

(% of Total Impurities)

| RE025 (Citric acid 3 mg) | Air infusion | $CO_2$ infusion |
|---|---|---|
| Starting Time | 0.07 | 0.11 |
| 25° C., 3 Month | 0.07 | 0.07 |
| 25° C., 6 Month | 0.1 | 0.08 |
| 40° C., 1 Month | 0.09 | 0.11 |
| 40° C., 3 Month | 0.69 | 0.24 |

TABLE 10

| RE026 (Citric acid 6 mg) | Air infusion | $CO_2$ infusion |
|---|---|---|
| (% of Total Impurities) | | |
| Starting Time | 0.06 | 0.1 |
| 25° C., 3 Month | 0.08 | 0.07 |
| 25° C., 6 Month | 0.2 | 0.1 |
| 40° C., 1 Month | 0.12 | 0.1 |
| 40° C., 3 Month | 0.7 | 0.28 |

Figure 2:
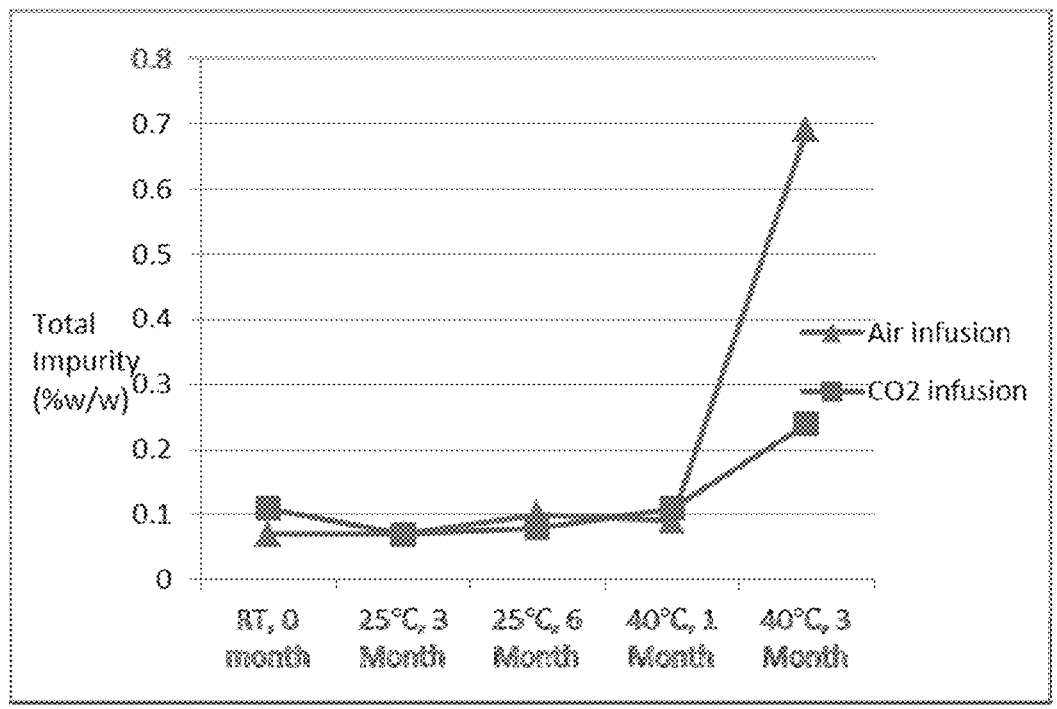
FIG. 2 shows the comparative stability data at room temperature and 40° C. for air-infused vs. $CO_2$-infused Formulation RE025 (3 mg citric acid).
Figure 3:
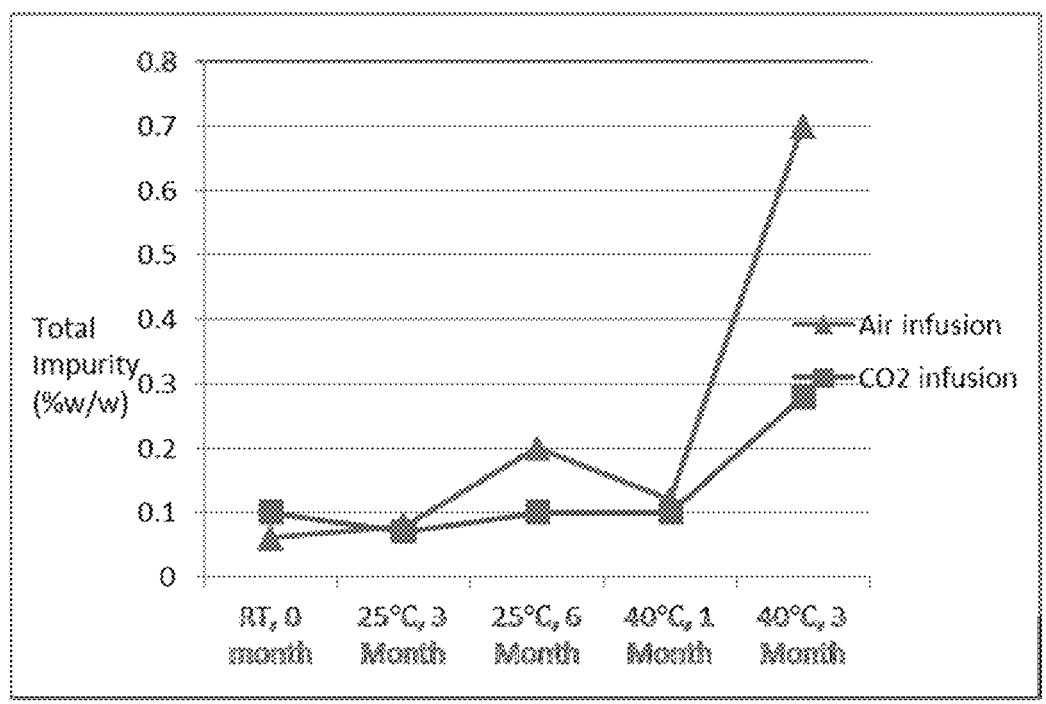
FIG. 3 shows the comparative stability data at room temperature and 40° C. for air-infused vs. $CO_2$-infused Formulation RE026 (6 mg citric acid).

The results of Tables 8-10 are plotted in FIGS. 1-3. The stability results show that adding citric acid 3 or 6 mg/mL in the formulation increased stability of the cabazitaxel formulation. The results also show that infusing $CO_2$ in the vial increased stability of cabazitaxel formulations, most noticeably after storage at 40° C. for 3 months.

We claim:

1. An enclosed liquid pharmaceutical composition container, comprising a liquid phase and an gaseous phase, wherein the liquid phase comprises cabazitaxel, polysorbate 80, ethanol, and one or more pH adjusters, the gaseous phase is saturated with $CO_2$, and the pH is about 3.0-4.0, before sealing of the container.

2. The enclosed liquid pharmaceutical composition container of claim 1, wherein the pH adjuster is carbonic acid and/or carbonate.

3. The enclosed liquid pharmaceutical composition container of claim 1, wherein the pH adjuster is citric acid and/or citrate.

4. The enclosed liquid pharmaceutical composition container of claim 1, wherein the pH adjusters are carbonic acid/carbonate and citric acid/citrate.

5. The enclosed liquid pharmaceutical composition container of claim 1, wherein the pH is 2.9-3.4.

6. The enclosed liquid pharmaceutical composition container of claim 1, wherein the liquid phase comprises 10-20 mg/mL cabazitaxel, 200-600 mg/mL polysorbate, 2-10 mg/mL citric acid, and 20-60% (w/v) ethanol.

7. The enclosed liquid pharmaceutical composition container of claim 6, wherein citric acid is about 6 mg/mL, cabazitaxel is about 10 mg/mL, and polysorbate 80 is about 260 mg/mL; or citric acid is about 6 mg/mL, cabazitaxel is about 20 mg/mL, and polysorbate 80 is about 520 mg/mL.

8. A process for preparing the enclosed liquid pharmaceutical composition container of claim 1, comprising the steps of:
   (a) mixing cabazitaxel, polysorbate 80, one or more pH adjusters, and ethanol to prepare a liquid pharmaceutical formulation,
   (b) filing the formulation into a container,
   (c) adding a sufficient amount of gaseous $CO_2$ to occupy the open space of the container, and
   (d) sealing the container.

9. The process according to claim 8, further comprising a step (0) before step (a):
   (0) preparing a pH adjuster of carbonic acid/carbonate by adding a sufficient amount of gaseous $CO_2$ to water until pH reaches about ≤5.

10. The process according to claim 8, wherein the one or more pH adjusters are carbonic acid/carbonate and citrate acid/citrate.

11. The process according to claim 10, where in step (a), polysorbate 80 is first mixed with the pH adjuster of carbonic acid/carbonate, and then cabazitaxel, citric acid, and ethanol is added.

12. The process according to claim 9, wherein the pH reaches about ≤4.

* * * * *